United States Patent [19]

Lazo de Zbikowski

[11] Patent Number: 4,612,921
[45] Date of Patent: Sep. 23, 1986

[54] EXTERNAL FIXATION SYSTEM FOR OSTEOSYNTHESIS

[76] Inventor: Juan Lazo de Zbikowski, Virgen des la Antigua, 10-1o -Sevilla, Spain

[21] Appl. No.: 748,831

[22] Filed: Jun. 26, 1985

Related U.S. Application Data

[62] Division of Ser. No. 448,330, Dec. 9, 1982, Pat. No. 4,541,422.

[30] Foreign Application Priority Data

Dec. 9, 1981 [ES] Spain .................................. 507.799

[51] Int. Cl.⁴ .............................................. A61F 5/04
[52] U.S. Cl. .................................. 128/92 A; 128/92 B
[58] Field of Search ................. 128/92 A, 92 R, 92 B, 128/92 E

[56] References Cited

U.S. PATENT DOCUMENTS

| | | | |
|---|---|---|---|
| 2,238,870 | 4/1941 | Haynes | 128/92 A |
| 2,346,346 | 4/1944 | Anderson | 128/92 A |
| 2,391,537 | 12/1945 | Anderson | 128/92 A |
| 4,135,505 | 1/1979 | Day | 128/92 A |
| 4,271,832 | 6/1981 | Evans et al. | 128/92 A |
| 4,308,863 | 1/1982 | Fischer | 128/92 A |
| 4,312,336 | 1/1982 | Danieletto et al. | 128/92 A |
| 4,360,012 | 11/1982 | McHarrie et al. | 128/92 A |
| 4,365,624 | 12/1982 | Jaquet | 128/92 A |
| 4,393,868 | 7/1983 | Teague | 128/92 A |
| 4,456,004 | 6/1984 | Kenny | 128/92 A |

Primary Examiner—Gene Mancene
Assistant Examiner—C. W. Shedd
Attorney, Agent, or Firm—Wender Murase & White

[57] ABSTRACT

An improved functional attachment system for osteosynthesis of the type having transfixion studs inserted into fractured bone fragments. The system has telescopic bars coupled with the studs by holding means. The transfixion studs have a spearhead on one end thereof with the base of the spearhead being wider than the stud diameter. In one embodiment, the holding means has articulated joints with jaws for attaching the telescopic bars and the studs thereto. In one embodiment the means for holding the telescopic bars is a pair of opposed plates which rotate in the concave cavity of a circular housing. Each plate has opposing elongated holes in which are attached a pair of opposing disks having diametrically opposed channels adapted for receipt of a telescopic bar. Screw means draw the plates and disks together for rigidly positioning a telescopic bar.

7 Claims, 27 Drawing Figures

EXTERNAL FIXATION SYSTEM FOR OSTEOSYNTHESIS

This is a division of application Ser. No. 448,330, filed Dec. 9, 1982, now U.S. Pat. No. 4,541,422.

BACKGROUND OF THE INVENTION

1. Field of the Invention

The present invention deals with some important improvements in the functional attachment system for osteosynthesis, preferably applicable to the osteosynthetic technique for external devices. The known techniques are the subject of Spanish Pat. No. 483.191 by the same inventor.

2. Description of the Prior Art

The system described in the aforementioned Spanish Pat. No. 483.191 is based on the mechanical or biomechanical principle consisting of the utilization of some sliding devices parallel to the damaged or fractured bone in such a way that the muscular contraction is converted into an impact or compression at the fracture focus between the fragments equal in magnitude and opposite to said contraction. A similar effect is produced by the action of muscle "tone," which is a state of minor permanent contraction, or by the action of gravity and load.

The principle is carried out whenever in external osteosynthesis use is made of mechanical devices that neutralize or tend to neutralize all angular, lateral or rotational movements, with movement in the direction of the longitudinal or major axis of the bone remaining free.

Hence this is osteosynthesis in which the "bridge," with a solid osseous anchor, is formed of one or more parts sliding together.

All current osteosynthetic systems are based on achieving absolute rest for the focus, and include those systems which maintain compression at the focus by means of endless screw systems, in order to increase stability; but in all these techniques, the compression is virtually invariable and its magnitude entirely empirical.

In the system under the Spanish Pat. No. 483.191 mentioned above, the magnitude of the compression is variable in relation to the function which, from least to greatest importance are muscular tone (rest); muscular contraction (movement); weight (bipedal standing); and dynamic load (walking; weight multiplied by acceleration).

External fasteners for the treatment of fractures, especially open and serious ones, comprise transfixion clips or studs which, by attaching to the two or more fragments of a fractured bone, unified externally relative to the bone by means of metal bars. These bars and the transfixing clips or studs are held together by holding means such as clamps articulated joints or ball-and-socket joints.

There are on the world market more than 50 models of external fasteners of various mechanical form but essentially having the same principles. In all of them, the joining bars are of two types.

1. Neutralizing bars. These are simple metal bars, generally steel, in several sections, for the most part cylindrical and of various diameters and lengths.

2. Compression bars. These are formed of endless-screw devices, blockable, that make it possible to apply compression by prestressing same and the entire system. When the endless screw is blocked, the pressure applied is theoretically maintained constant.

There are models in which the pressure is exerted not by a screw but by rubber bands or springs.

The functional attachment system for osteosynthesis constituting the reason and basis for Spanish Pat. No. 483.191 is based on giving the bars a telescopic arrangement, sliding together according to the simplest prototype formed by a double tube in which the exterior is greater in diameter and with an internal diameter equal to the outside of the interior.

When each of these telescopic parts is made solid with the two fragments of a fracture by means of appropriate clamps or ball-and-socket joints and this bar is placed parallel to the major axis of the bone, an axial compression is produced in the area of the fracture by the action of the muscles. It should be pointed out here that the muscle is never completely relaxed, but rather even in this state maintains a degree of permanent contraction called muscle "tone." That is, the fracture remains subjected to a permanent compression by this muscle "tone," but variable at all times in relation to position and function.

Said telescopic sliding bars, while maintaining longitudinal movement, cancel out angular, rotational and other movements that are harmful to the healing of the fracture.

By means of the functional attachment system set forth in the aforementioned Spanish patent, it is possible to utilize mechanical compression stimuli on the focus that are of physiologically vary magnitude corresponding to muscular tone, muscual contraction, static load and dynamic load.

In general terms, most of the presently existing fastener systems for osteosynthesis consist of a number of elements or parts with which each total assembly is constructed; these elements or parts may be quite varied, as for example single, double, double in a square, in a triangle, in double square or irregular, these terms corresponding to the number of bars used and the location of same in space. The diversity of types and locations of fractures makes it possible to use in each case the most appropriate assembly in relation to the type of fracture and mechanical needs of each situation.

SUMMARY OF THE INVENTION

The improvements under the invention are aimed at perfecting the technique of the functional attachment system for osteosynthesis, advantageously modifying the means and systems provided for the application and development of the system known under the aforementioned Spanish Pat. No. 483.191, said improvements consisting essentially of the following.

The end or sharp point of the transfixion stud is given a spearhead shape with cutting edges angled such that they favor easy penetration into the bone. In addition, the end or base of the spearhead proper is given a diameter slightly larger than the rod, shaft or body that follows, thus favoring the penetration of said rod and the remainder of the stud body; the latter's ability to penetrate is increased by means of two mortices on opposite sides immediately after the end of the spearhead.

Another important improvement introduced in the transfixion studs consists of making several lengthwise grooves in the threaded area, passing perpendicularly through the threads, thus giving the stud self-threading properties.

A single diametrical distal hole is made in telescopic compression bars (biocompressors) in the encircling part for the purpose of providing an outlet for air and allowing lubrication; in this hole is housed a fastening pin to prevent movement of the encircled bar while the apparatus is assembled and when the proper arrangement of the part is checked later.

The ends of these telescopic comression bars (biocompressors) are roughened to improve the grip of the device's jaws on them.

In one of the types of jaws for the system, the rods perpendicular to the grasping plates are joined solidly and rigidly to promote speed in applying the system.

In the other type of jaw for grasping the transfixion studs, a sort of housing with a circular foot has been incorporated on the upper plate, with a seat supporting two plates able to rotate and oscillate at the same time, each of these supporting a jaw disk provided on one side with a semicircular mortice for seizing the sliding bar, while on the other side there is an axis point housed in a respective hole in the corresponding plate which, as it is vertically extended, allows the claw disk to move vertically and rotationally. In addition, these two plates supporting the claw disks that seize the sliding bar are joined by screw means with a wing nut and a prismatic head, with the particularity that the threading on one of the plates is achieved on a female part or nut mounted on the plate to oscillate and inside a spacious hole in which it can oscillate by means of two axis points. This set of jaw elements favors the perfect alignment and parallelism of the sliding bars, shortening the assembly time for the device used in the system, better guaranteeing the unit's parallelism.

In the articulated or rotating joints and between the two facing plates between the jaw assemblies is inserted a washer of any relatively soft material, such as polyvinyl, while on the neutralizing bars one of the ends is roughened to prevent slippage of the bar on the jaw.

The device is completed with a punch comprising simply a rod with a point and a shaft, this utensile serving to expand the parts of the ball-and-socket joint or jaw.

Another complementary utensil intended to protect the soft parts is also incorporated into the apparatus, this comprising a type of punch with a shaft and a tube with a collar at one end and at the other a mortice or cavity formed by two points. This utensil serves to prevent the possibility of aggression against the muscle by the threaded part of the transfixing studs.

On the auxiliary guide for placement of the transfixion studs, the holes existing between the two plates that clasp the studs are extended horizontally with grooves on both sides of the central channel to allow the passage of the spearhead of the transfixion keys with no need to open them.

It also includes a bar alignment guide consisting of two members plates or bars with with a curved mortise on the head of its lower end which will rest on the bars, a head at its upper end which allows perpendicular and transversal passage of a rod attachable by means of a prisoner screw, while said rod is rigidly joined to the head of the other vertical plate or bar.

There is also a brace having low expansion of its reducing gears to activate the transfixing studs and, finally, a T-shaped wrench with a head to act as a percussion hammer on the studs in the first phase of bone perforation and with nut and tube wrenches at the other ends of its arms.

So that the foregoing will be more clearly understandable, drawings are attached representing one example of realization of an external attachment apparatus constituted according to the invention, without this assuming that the invention is limited to only this example, given that modifications are possible to adapt the system to the various situations that may arise.

BRIEF DESCRIPTION OF THE DRAWINGS

Said drawings show the following:

FIG. 7. Perspective view of a possible variant of the compression bar.

DESCRIPTION OF THE PREFERRED EMBODIMENTS

Figure 1:
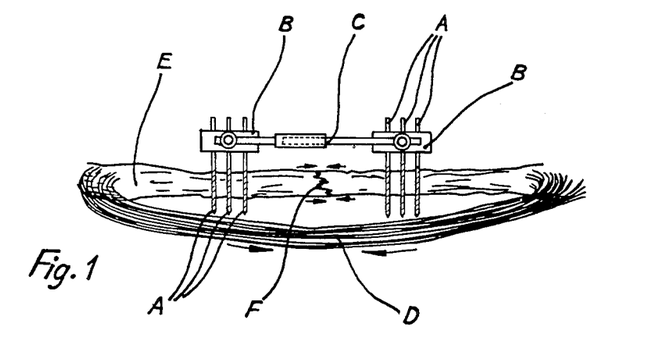
FIG. 1. Diagram of the principle on which the invention's system is based.

The description of the example of the apparatus and parts shown in the aforementioned figures is as follows:

In FIG. 1, which shows a diagram of the principle on which the invention's system is based, A designates some transfixion studs or clips that pass through and grasp both fragments of the fractured bone E and makes them externally solid with one another by means of telescopic metal bars C that are in turn joined by means of the jaws B in such a way that the device makes it possible for the contraction of the muscles D to be converted into an impacting or compression between the fragments at the focus of the fracture F that is equal in magnitude and opposite to said contraction.

Figure 2:
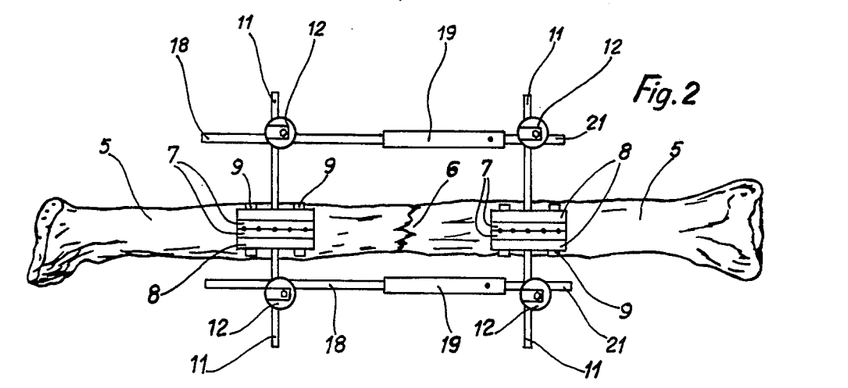
FIG. 2. Lateral elevation of an external attachment apparatus, double square.
Figure 3:
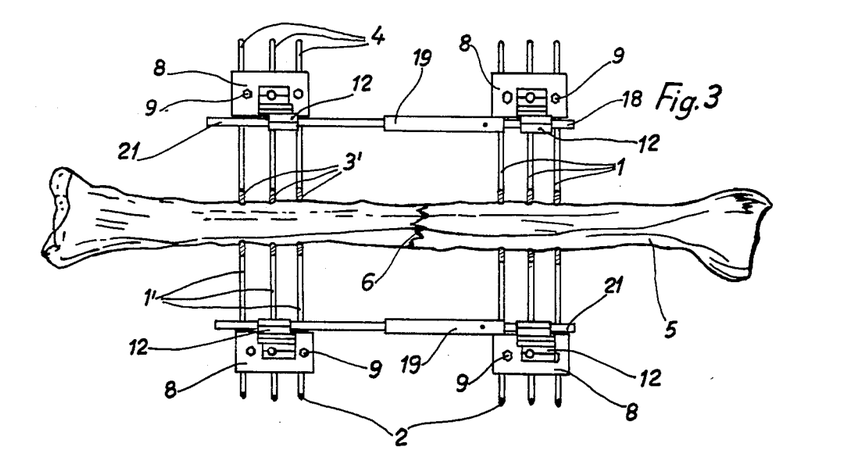
FIG. 3. Bottom of the apparatus in FIG. 2.

FIGS. 2 and 3, which, as has already been stated, show a lateral elevation and a bottom view of an external, double-square attachment device applied to a fractured bone -5- with a fracture -6-, show the various mechanical parts and elements of the device which will be described in detail below, with the same numerical references.

The example to which we are referring utilizes some transfixion studs designated by -1-, shown in FIGS. 3, 4, 4a, 4b and 4c, which consist of some rods with a sharp, cutting and triangular point -2-, an area of thread spirals -3'- located in the center and the prism-shaped end -4- for applying the wrench or brace 43. It should be noted that said sharp point -2- is flattened with two opposite plane faces and two mortices -2'- together with which the base of the triangle forming the point is very broad and extends on both sides, by which it favors penetration of the stud shaft in the bone. In the threaded area -3'- there are three lengthwise grooves -4'- that pass perpendicularly through the thread spirals and confer self-threading properties on the stud.

Figure 4:
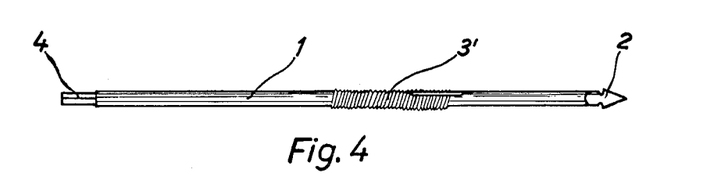
FIG. 4. View of a transfixion stud.
Figures 4A, 4C, 4D:
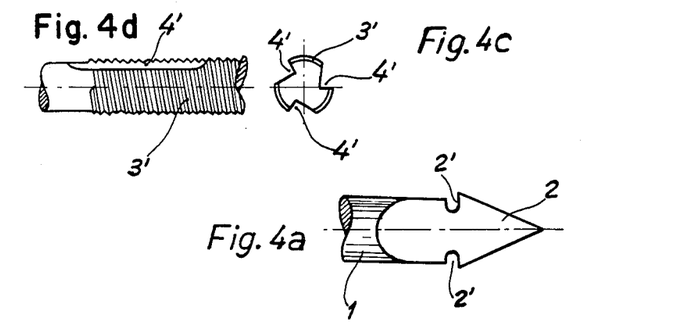
FIG. 4a. Enlarged detail from the bottom of the point of the transfixion stud in FIG. 4.
FIG. 4c. Transversal cross-section of the threaded area of the stud in FIG. 4.
FIG. 4d. Enlarged detail of the threaded area of the stud in FIG. 4.
Figure 4B:
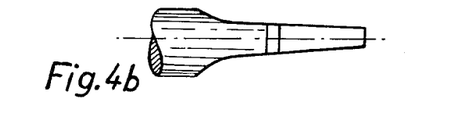
FIG. 4b. Enlarged detail, side view, of the point of the transfixion stud in FIG. 4.

The transfixion studs 1' are introduced and thread themselves into the bone -5-, remaining protruding through the skin in order to allow external assembly of the rest of the elements.

In the example in FIGS. 2 and 3, six transfixion studs -1- are used, threaded into the bone -5-, three on one side of the fracture -6- and three on the other.

Figures 8, 9, 10, 10A:
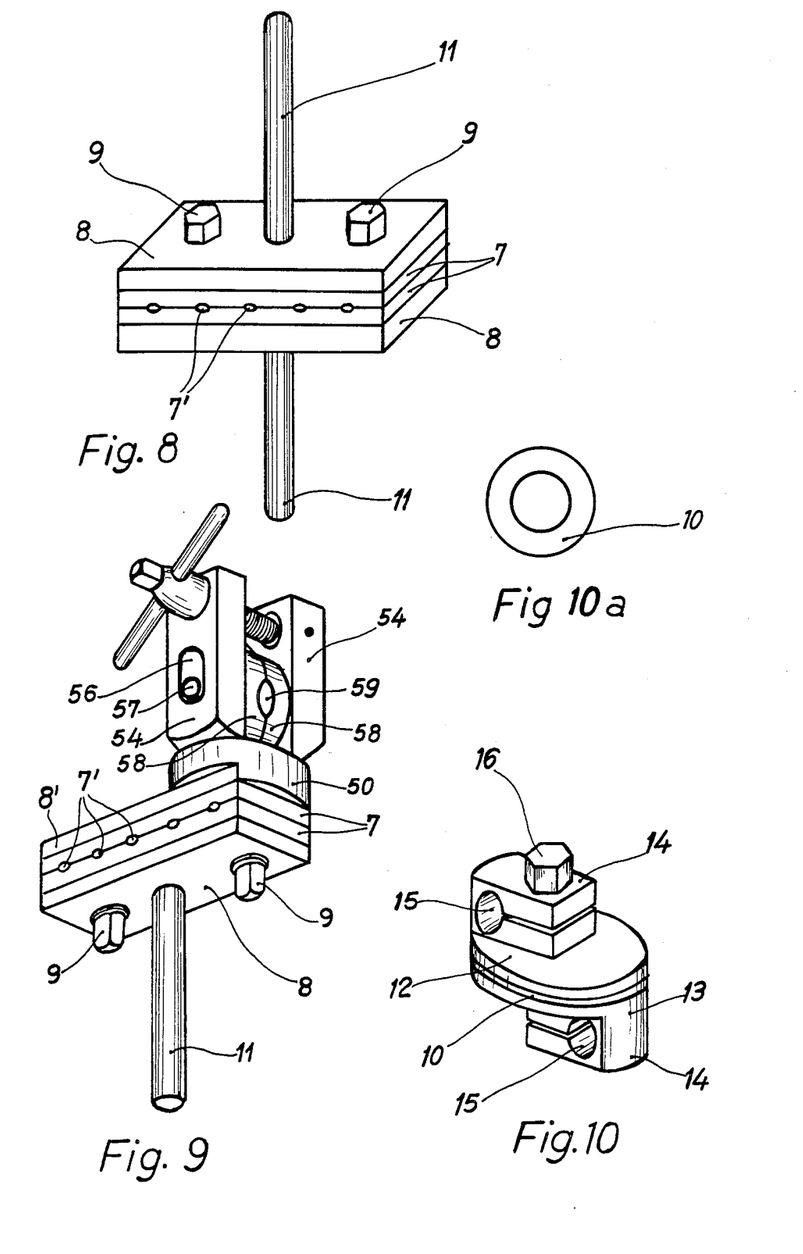
FIG. 8. Perspective view of one type of jaw with its rods solid with the plates.
FIG. 9. Perspective view of another type of jaw for seizing the sliding bars.
FIG. 10. One of the ball-and-socket joints, seen in perspective.
FIG. 10a. Washer for the ball-and-socket joints.
Figure 9A:
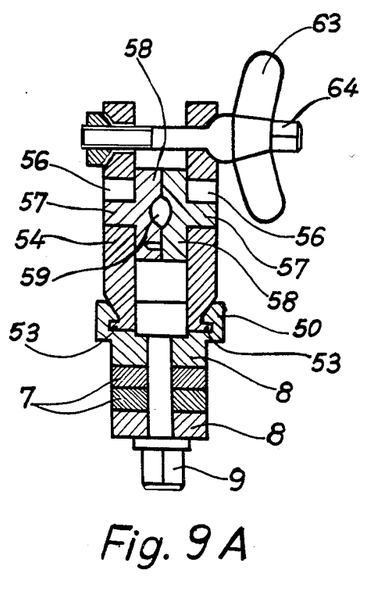
FIG. 9a. Section of the jaw in the previous figure.
Figure 9B:
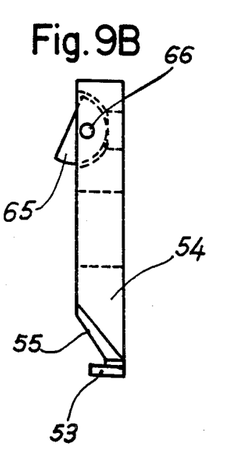
FIG. 9b. Lateral and view of one of the supports of the claws of the jaw in FIG. 9.
Figure 9C:
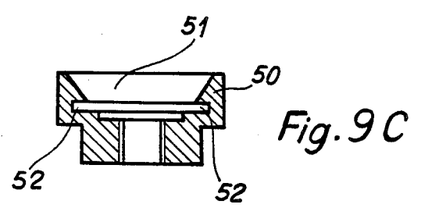
FIG. 9c. Section of the seat and base of the jaw supports in FIG. 8.
Figure 9D:
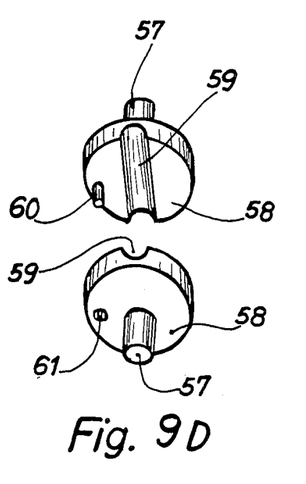
FIG. 9d. Perspective view of the two grasping claws of the jaws.
Figure 9E:
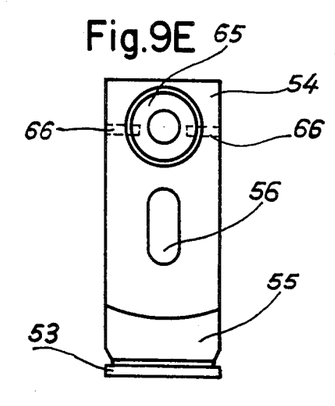
FIG. 9e. Profile view of one of the supports of the claws of the jaw in FIG. 9.

Each group of three of the aforementioned transfixion studs -1- is held by two jaws -8- near both ends (FIG. 3). Each one of these jaws -8- consists of two small fiber plates -7- between two metal plates -8-, all this joined by two hexagonal-head screws -9-. The small fiber plates -7- have some transversal grooves -7'- which, when brought together, serve as a seat for the studs -1-. In this type of jaws, the upper and lower bars -11- are solid and perpendicular with their respective plates -8- (FIG. 8).

The apparatus includes some ball-and-socket joints designated by -12- (see FIG. 10), of the universal type, consisting of two disks -13- with their faces in contact grooved, and interposed between them a polyvinyl washer -10- (FIG. 10a), each disk being provided with a semidivided, flexible projection -14- with a hole -15- for the passage of the bars -11- solid with the plates -8-, in addition to the telescopic, sliding bars 18 and 21, said two disks being joined by the screw -16- by means of which the articulated joint is grasped by the aforementioned bars.

Figure 17:
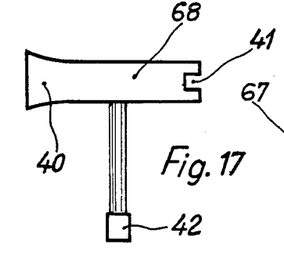
FIG. 17. Hammer wrench.

The joining bars are of two types, one -17- as shown in FIG. 17 that is a simple cylindrical steel bar of variable length, usable as a neutralizing bar and one roughened end -17'-.

Figure 5:
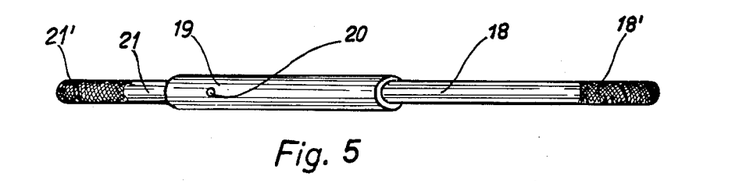
FIG. 5. Perspective view of one of the compression bars (biocompressors).
Figure 6:
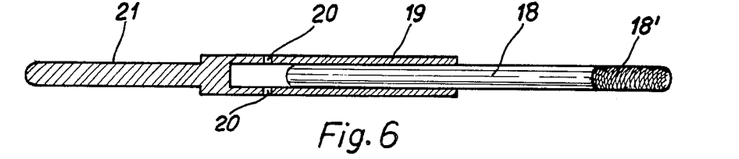
FIG. 6. Longitudinal section of the compression bar in FIG. 5.

The others, which we shall call biocompressors, are those shown in detail in FIGS. 5, 6 and 7. They consist of a cylindrical bar -18-, like -17-, and also with one end -18'- roughened, but shorter, and a tube -19- closed at one of its mouths or ends, which extends into a long cylindrical shaft -21- of the same diameter as the bar -18-, with the end -21'- roughened. The tube -19- has a suitable inner diameter so that it can house the bar -18- inside it, with the bar sliding longitudinally in telescopic fashion, with a transversal hole -20- for lubrication and as a housing for the clip pin -23- which will be utilized during assembly of the system.

Simple systems will not be able to utilize the extensible bar described above as they carry a single bar that would give rise to rotational movements. Because of this, the use of variants is provided for in which the portion of the sliding bar housed in the tube has a prismatic cross-section, such as triangular, squared or some other category of polygon. In this regard FIG. 7 shows an extensible bar -18''- with a triangular portion -22-, for which reason the tube -19'- will also have a cavity with the same triangular cross-section. The end of this sliding bar -18''- will also have a roughened area -18'-.

FIGS. 9, 9a, 9b, 9c 9d and 9e show a jaw like the one in FIG. 8 with the corresponding bar -11- fixed and perpendicular to the lower plate -8-, while on the upper plate -8'- there is mounted a device for grasping the telescopic sliding bars -8-, -21-. This device includes a circular housing -50- which, on the walls of the concave cavity -52-, has an inner circular expansion or groove -52- intended to receive the flanges -53- present on one side of the end of the housing plates -54- which have, next to their respective flanges -53- a convex-surfaced recess -55- suitable for seating in the concave cavity -51- and able to turn in it, its rotation guided by the flanges -53- on the grooves -52-. Each plate -54- defines a vertically elongated hole -56- which face one another, these holes being intended to receive the axis points or stub shafts -57- of two disks -58- provided with diametrical channels or grooves -59- having a semicircular cross-section to seize and grasp between them the bars -18- and -21-, -60- being a shaft solid with one of the disks intended to be introduced into the hole -61- of the other so that their channels or grooves are always facing one another.

Once the plates -54- are seated in the housing -50-, with the disks -58- supported by their axes -57- in the holes -56- and with the respective bars -18-, -21- grasped between the channels -59-, both plates will be joined by screw means such as screw -62- with one manual wing nut -63- and another prismatic -64- to activate it with a wrench. The roughened area of the screw -62- threads itself into a nut -65- which on the outside has the shape of a cap, loosely housed in a cavity in one of the plates -54- where it is mounted by means of two axis points -66- that enable it to oscillate so that the joining of the two plates -54- forced by the screw -62- is not rigid but rather articulated.

Figures 11, 12:
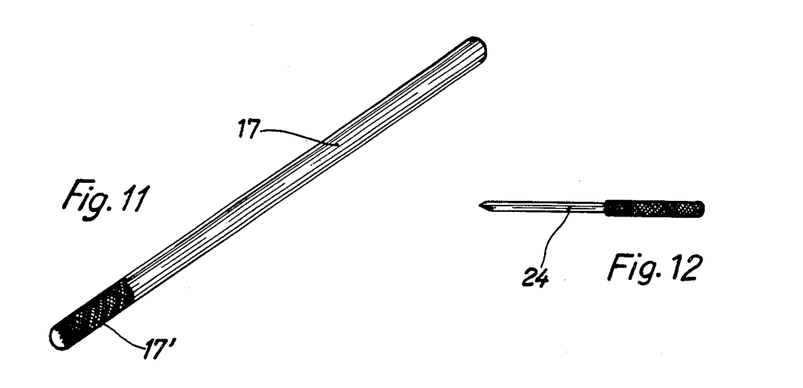
FIG. 11. One of the neutralizing bars.
FIG. 12. Punch.

FIG. 12 shows a punch -24- that makes it possible to expand or separate the parts -13- and -14- of the jaws -12- shown in FIG. 10 when it is introduced into the holes -15-.

Figure 13:
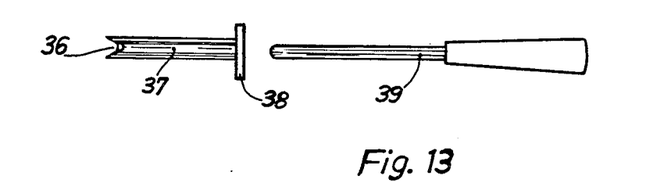
FIG. 13. Protector for soft parts and pin.

In FIG. 13 there is another type of punch -39- with its corresponding handle, and a tubular body -37- with a collar -38- at one end and at the other end a double-pointed opening -36-, this being a protector of soft parts and clip that is incorporated into the apparatus to prevent the possibility of aggression against the muscle by the roughened part of the transfixing studs.

Figure 14:
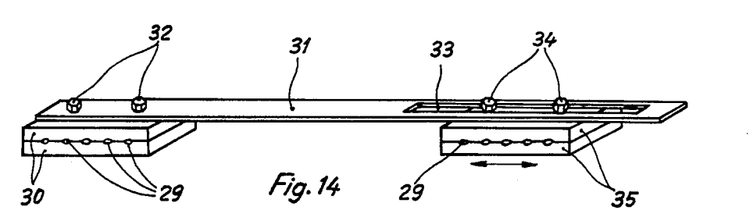
FIG. 14. Auxiliary guide for placement of the transfixion studs.

Placement of the external fasteners under the invention must be very precise, and in order to facilitate their proper placement some special instruments have been devised, one of which is shown, also by way of example, in FIG. 14. This is a guide for the anchoring parts and for the transfixing studs -1- (FIG. 14) that makes it possible to place said parts and studs, housing them between the grooves -29- in the two facing plates -30- forming a jaw, attached at one end of the plate -31- by means of the screws -32- which in turn regulate the pressure of said two plates. At the other end of the plate -31- there is an elongated hole -33- in which can be set in variable positions the heads of the screws -34- that hold the other two grooved plates -35-, forming another jaw to hold the transfixion studs or parts -1- between the grooves -29-. In this way, said studs or parts -1- can be placed parallel to one another in the fragments of the bone -5-, on either side of the fracture -6-. It must be pointed out that the grasping grooves -29- of the studs -1- have a semicircular central channel and an expansion on either side, which when brought together results in a horizontally elongated hole allowing passage of the point -2- of the transfixion studs -1- with no need to separate the plates -30-, -35-. These guides will be of various sizes for studs and parts of various diameters.

Figure 15:
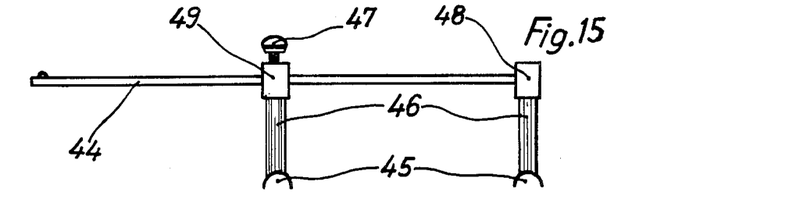
FIG. 15. Bar alignment guide.

The device likewise includes as auxiliary element another guide, an example of realization of which is shown in FIG. 15, intended to mount the sliding compression bars -18-, -21- in an arrangement exactly parallel to one another. It consists of two vertical members, tubes or bars -46- with their lower end -45- with a concavely curved plate to rest upon the bars, while the upper end or head -48- of one of them is solid with the perpendicular bar -44-, which bar can slide through the head -49- where there is a prisoner screw -47- to fix the bar -44- in the appropriate position, once parallelism has been achieved for the bars -18-, -21- on which this guide rests.

Figure 16:
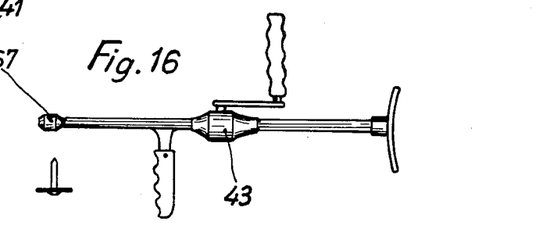
FIG. 16. Low-extension brace.

As for the brace -43- shown in FIG. 16, it is not necessary to describe it, as this is a brace of known type, with the sole requirement that its rotating head -67- which is what coupled with the end -4- of the transfixing studs -1'-, rotates slowly, i.e., that its reducing gears are of low expansion so that the perforation of the bone, by rotation of the stud, can be achieved comfortably and without effort.

Another complementary element consists of the hammer-wrench adjustment tool -68-, shown by way of example in FIG. 17. It has a "T" shape and at the end of one arm it has a broad head -40- for percussion on the end of the studs -1'- in the first phase of bone perforation; an opening -41- at the opposite end of said arm to grasp the nuts; and a tube-wrench opening -42-, also to grasp the nuts.

In order to improve the mechanical conditions of the sliding surfaces of the telescopic bars -18- and -21-, the use of low-friction materials such as metal-polyethylenes, metal-ceramics and others with similar properties, has been provided for.

The functional attachment system for osteosynthesis by means of biocompressors, which has been described, and the external attachment apparatus created according to said system, which has been shown and described as an example of realization of the invention, may be varied in constructive details of a secondary nature, such as size, shapes, materials, numbers of parts and other particularities that do not alter the essence of the invention, which is summarized in the following claims.

I claim:

1. An improved functional attachment system for osteosynthesis of a fractured bone having a bone fragment on either side of a fracture site of the fractured bone comprising:

at least one elongated transfixion stud for insertion into each bone fragment, having a shaft, one end of said shaft having a spearhead configuration with two planar faces which form cutting edges for penetration of the bone, said spearhead end having a base opposite said cutting edges, said base being wider than a diameter of said shaft, and opposed notches extending between said two planar faces and said shaft;

at least one telescopic bar aligned generally parallel to a longitudinal axis of the fractured bone, having an outer telescopic tubular member and an inner telescopic member slidably inserted into said outer telescopic member, said outer telescopic member having a transverse hole therein for venting air trapped between said telescopic members and for entry of lubricant therebetween, and a fastening pin for insertion into said outer telescopic member hole for restriction of sliding insertion of said inner telescopic member into said outer telescopic member; and means for holding said transfixion studs and said telescopic bars, said means having articulated joints coupled to said telescopic bars, said joints having jaws for attachment to said transfixion studs.

2. The improvements as recited in claim 1 wherein said stud shaft has a threaded portion and grooves cut through said threads generally parallel to an axis of said shaft so that said transfixion stud is self-threadingly engageable in the bone fragment.

3. The improvements as recited in claim 1 wherein:

said outer and inner telescopic members have noncircular cross-sections and ends with a roughened surface finish for coupling with said articulated joints; and said means for holding said transfixion studs includes a pair of opposing joint jaws for coupling with one of said telescopic bar roughened ends and a washer interposed between said joint jaws, constructed of material which is softer than the material of said joint jaws.

4. The improvements as recited in claim 1 wherein said means for holding said transfixion studs is a pair of opposed holding plates for holding the studs therebetween, and a holding plate stud is rigidly and perpendicularly attached to one of said holding plates for connection to other elements of said holding means.

5. The improvements as recited in claim 1 wherein said jaws for holding said transfixion studs have an upper plate attached to one of said jaws;

said upper plate has a device for holding said telescopic bars having a circular housing defining a concave cavity with a circular groove therein, a pair of opposed housing plates, each plate having a flange adapted for cooperation with said cavity groove such that said housing plates are rotatable in said groove and captured relative to an axis of rotation, said housing plates having a convex surface adapted for contact with said housing cavity, an elongated hole defined by each housing plate, said elongated holes being slot means which permit rapid parallel alignment of said telescopic bars, a pair of opposing disks having diametrically opposed channels on inner faces thereof, adapted for receipt of a telescopic bar and stub shafts on outer faces thereof adapted for slidable and rotatable insertion into elongated holes of said housing plates; and screw means attached to said two housing plates for drawing said plates and said disks together, thereby rigidly positioning a telescopic bar relative to said device for holding said transfixion studs.

6. A kit of components for constructing an improved functional attachment system for osteosynthesis of a fractured bone having a bone fragment on either side of a fracture site of the fractured bone comprising:

at least one elongated transfixion stud for insertion into each bone fragment, having a shaft, one end of said shaft having a spearhead configuration with two planar faces which form cutting edges for penetration of the bone, said spearhead end having a base opposite said cutting edges, said base being wider than a diameter of said shaft, and opposed notches extending between said two planar faces and said shaft;

at least one telescopic bar aligned generally parallel to a longitudinal axis of the fractured bone, having an outer telescopic tubular member and an inner telescopic member slidably inserted into said outer telescopic member, said outer telescopic member having a transverse hole therein for venting air trapped between said telescopic members and for entry of lubricant therebetween, and a fastening pin for insertion into said outer telescopic member hole for restriction of sliding insertion of said inner telescopic member into said outer telescopic member;

means for holding said transfixion studs and said telescopic bars, said means having articulated joints coupled to said telescopic bars, said joints having jaws for attachment to said transfixion studs;

a protector for prevention of tissue damage from insertion of said transfixion studs into said bone fragment having a tube for insertion of said transfixion stud therethrough, said tube having a collar on one end thereof and double-point projections on a second end thereof, and a handled punch for slidable insertion into said tube for introduction of said tube into a patient's body prior to insertion of said transfixion stud therein;

an alignment guide for parallel alignment of said telescopic bars having two members, each member having a curved portion for contact with a telescopic bar and heads, said heads adapted for receipt of a rod, one of said heads having rigid connection to said rod and the other of said heads having a prisoner screw for selective adjustment of distance between said heads.

7. The kit as recited in claim 6 further comprising a T-shaped adjustment tool having a hammer head on one leg thereof for hammering osteosynthesis components and wrenches on the other two legs thereof for adjustment of the osteosynthesis components.

* * * * *